United States Patent [19]

Kurono et al.

[11] Patent Number: 5,110,945

[45] Date of Patent: May 5, 1992

[54] 1-AZONIABICYCLO[3.3.0]OCT-1(5)-ENE SALT DERIVATIVES AND PROCESS FOR THE PREPARATION OF THE SAME

[75] Inventors: Masayasu Kurono; Yasuaki Kondo; Yukiharu Matsumoto; Mitsuru Oka; Kiichi Sawai, all of Nagoya, Japan

[73] Assignee: Sanwa Kagaku Kenkyusho Co., Ltd., Aichi, Japan

[21] Appl. No.: 776,039

[22] Filed: Oct. 15, 1991

[30] Foreign Application Priority Data

Oct. 16, 1990 [JP] Japan ................................ 2-275216

[51] Int. Cl.$^5$ ........................................... C07D 487/04
[52] U.S. Cl. ................................................... 548/453
[58] Field of Search ........................................ 548/453

[56] References Cited

FOREIGN PATENT DOCUMENTS 61-229893 10/1986 Japan.
61-254587 11/1986 Japan.
62-16487 1/1987 Japan.

OTHER PUBLICATIONS

Miyano et al. "Synthesis", p. 701, Sep. 1978.
Miyano et al. "J. Heterocyclic Hem.", vol. 19, p. 1465, Nov.-Dec. 1982.
Miyano et al. "J. Org. Chem.", vol. 46, p. 1737, 1981.

*Primary Examiner*—David B. Springer
*Attorney, Agent, or Firm*—Armstrong, Nikaido, Marmelstein, Kubovcik and Murray

[57] ABSTRACT

There are described 1-azoniabicyclo[3.3.0]oct-1(5)-ene salt derivatives inclusive of 1-azonia-4,6-dimethylbicyclo[3.3.0]oct-1(5)-ene perchlorate, and a process for the preparation of the same. The derivatives can be prepared by heating dicyclopropylmethanimine salt derivative in a solvent, in the presence or absence of an ammonium salt. Each of the derivatives is employed as an intermediate for preparing various medicines and agricultural chemicals.

3 Claims, No Drawings

1-AZONIABICYCLO[3.3.0]OCT-1(5)-ENE SALT DERIVATIVES AND PROCESS FOR THE PREPARATION OF THE SAME

BACKGROUND OF THE INVENTION

1. Field of the Invention

The present invention relates to a 1-azoniabicyclo[3.3.0]oct-1(5)-ene salt derivatives and a process for the preparation of the same. The derivative is useful as an intermediate for synthesizing various medicines and agricultural chemicals.

2. Related Arts

According to a conventional method, 1-azoniabicyclo[3.3.0]oct-1(5)-ene salt derivatives shall be prepared by reacting γ-butyrolactone with potassium cyanate, heating the resulting γ-(N-2-pyrrolidinonyl) butyric acid in the presence of soda lime, and then reacting the resulting 1-azabicyclo[3.3.0]-4-octene with perchloric acid [Miyano et al "Synthesis", page 701 (1978)]. As a method for preparing the intermediate of γ-(N-2-pyrrolidinonyl) butyric acid, such a method has also been proposed that 2-pyrrolidone is reacted with metallic sodium and then reacted with γ-butyrolactone [Miyano et al "J. Heterocyclic Chem.", Vol. 19, page 1465 (1982)].

The conventional processes given above shall be shown, as follows.

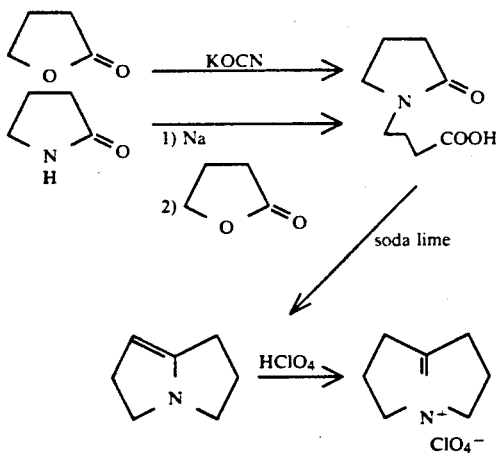

The conventional processes have following disadvantages. Namely, the first step for reacting γ-butyrolactone with potassium cyanate to synthesize γ-(N-2-pyrrolidinonyl) butyric acid requires high reaction temperature (about 200° C.) and provides a low yield (about 40%). While, the method of reacting 2-pyrrolidone with metallic sodium and then reacting with γ-butyrolactone may cause an abnormal reaction of accidental explosion.

The second step of the conventional process, namely for heating γ-(N-2-pyrrolidinonyl) butyric acid in the presence of soda lime to synthesize 1-azabicyclo[3.3.0]-4-octene has also disadvantages of that high reaction temperature (250°-300° C.) is require, and that the reaction product has a low stability.

SUMMARY OF THE INVENTION

The first object of the invention, therefore, is to provide a process for synthesizing 1-azoniabicyclo[3.3.0]oct-1(5)-ene salt derivatives, which can be widely applied for preparing various derivatives, is easy in operation, shows no risk of explosion, does not require expensive reagents and thus is suitable for the production of the derivatives in an industrial scale.

The second object of the invention is to provide novel 1-azoniabicyclo[3.3.0]oct-1(5)-ene salt derivatives which are different from the known salt [Miyano et al "J. Org. Chem.", Vol. 46, page 1737 (1981)] in physicochemical properties (partition coefficient, basicity, molecular refractive index, molecular conformation and the like) and thus to bring possibilities of an improvement in pharmacological properties (increase of activity, decrease of toxicity and the like) or of discoveries of new biological activity for 2-oxypyrrolidine compounds [Jap. Pat. No. Sho 61 (1986)-254587(A)], organoplatinum complexes [Jap. Pat. No. Sho 61 (1986)-229893(A)], cephalosporin derivatives [Jap. Pat. No. Sho 62 (1987)-16487(A)] and the like.

According to the invention, the first object can be attained by a process for the preparation of 1-azoniabicyclo[3.3.0]oct-1(5)-ene salt derivatives of the formula

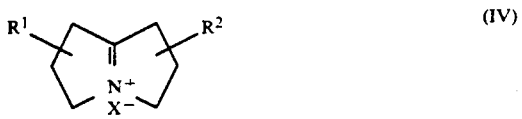

wherein X is a halogen atom, $ClO_4$, $NO_3$, $BF_4$, $R^3SO_3$, $(SO_4)_{0.5}$ or $CW_3CO_2$ [$R^3$ is a hydrocarbon group with 1-10 carbon atoms, and W is hydrogen or halogen atom], and $R^1$ and $R^2$ are same or different and each being hydrogen atom or hydrocarbon group with 1-10 carbon atoms, which comprises step of heating in a solvent a dicyclopropylmethanimine salt derivative of the formula

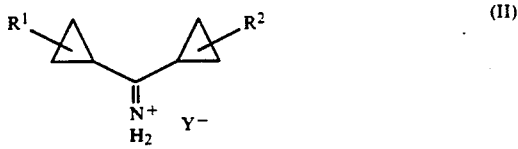

wherein $R^1$ and $R^2$ have the meanings as referred to, and Y is a halogen atom, $ClO_4$, $NO_3$, $BF_4$, $R^3SO_3$, $(SO_4)_{0.5}$ or $CW_3CO_2$ [$R^3$ and W have the meanings as referred to], solely or with an ammonium salt of the formula

wherein Z is a halogen atom, $ClO_4$, $NO_3$, $BF_4$, $R^3SO_3$, $(SO_4)_{0.5}$ or $CW_3CO_2$ [$R^3$ and W have the meanings as referred to] and $R^4$ is a hydrogen or hydrocarbon group with 1-10 carbon atoms, in case of that the symbol Y represents the halogen atom, $R^3SO_3$ or $(SO_4)_{0.5}$; or with the ammonium salt of Formula (III), wherein Z is the halogen atom, $R^3SO_3$ or $(SO_4)_{0.5}$, in case of that Y represents the radical other than the halogen atom, $R^3SO_3$ or $(SO_4)_{0.5}$, and the problems in the prior arts can be dissolved.

In the compounds shown by Formulae (II), (III) and (IV), chlorine, bromine and iodine atoms can be listed as the halogen atoms. The hydrocarbon group for substituents $R^1$, $R^2$, $R^3$ and $R^4$ can be an alkyl or aryl group. As the straight chain alkyl group, there can be listed those having 1-10 carbon atoms, such as methyl, ethyl, n-propyl, n-butyl, n-pentyl, n-hexyl, n-decyl and the like radicals. As the branched chain alkyl radicals, there can be listed such as i-propyl, i-butyl, sec-butyl, tert-butyl, i-pentyl and the like radicals. As the cycloalkyl group, there can be listed those having 3 or more carbon atoms, such as cyclopropyl, cyclobutyl, cyclopentyl, cyclohexyl, cycloheptyl and the like radicals. As the aryl group, there can be listed phenyl, tolyl, xylyl, mesyl and the like radicals.

The compounds shown by Formula (IV), wherein the substituent Y is the halogen atom, $R^3SO_3$ or $(SO_4)_{0.5}$, can be prepared by stirring the compound (II) in a solvent at temperature of 50°–100° C., or adding 1–10 equivalents of the compound (III) based on 1 equivalent of the compound (II) and stirring in a solvent at temperature of 50°–100° C. The compounds shown by Formula (IV), wherein the substituent Y is the radical other than halogen atom, $R^3SO_3$ or $(SO_4)_{0.5}$, can be prepared by adding to the compound (II) the compound (III), wherein Z is the halogen atom, $R^3SO_3$ or $(SO_4)_{0.5}$, and stirring in a solvent at temperature of 50°–100° C. In any case, the reaction completes by 1–24 hours. As the solvent, methanol, ethanol, n-propanol, i-propanol or the like alcohol, and a polar solvent such as dimethylsulfoxide, N,N-dimethylformamide, acetonitrile and the like can be used. The compound (IV) can be obtained by distilling out the solvent from the reaction mixture and recrystalizing with use of an alcohol such as ethanol, n-propanol, i-propanol, n-butanol, i-butanol or the like.

The dicyclopropylmethanimine salt derivatives (II) as the raw material can easily be synthesized by reacting a cyclopropylnitrile derivative with a cyclopropyl lithium derivative [R. P. Dion "Diss. Abstr. Int. B", Vol. 45, page 874 (1984)] and then converting the reaction product into its salt, or by reacting dicyclopropyl ketone derivative with ammonia in the presence of titanium tetrachloride and then converting the product into the salt.

The second object as referred to can be attained by 1-azonia-4,6-disubstituted-bicyclo[3.3.0]oct-1(5)-ene salts shown by the Formula of

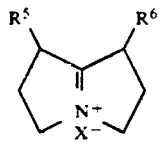

(I)

wherein X has the meaning as referred to, and $R^5$ and $R^6$ are same or different hydrocarbon group with 1–10 carbon atoms, or one of $R^5$ and $R^6$ represents hydrogen atom and the other is the hydrocarbon group with 2–10 carbon atoms.

Namely, the compounds shown by Formula (I), for instance 5-cyano-4,6-dimethyl-1-azabicyclo[3.3.0]octane which can be synthesized by starting from 1-azonia-4,6-dimethylbicyclo[3.3.0]oct-1(5)-ene perchlorate and applying a method known per se [Miyano et al "Synthesis", page 701 (1978)] shows a partition coefficient increased by 1.32 (theoretical) than that of 5-cyano-1-azabicyclo[3.3.0]octane which can be synthesized by starting from 1-azoniabicyclo[3.3.0]oct-1(5)-ene perchlorate and utilizing the similar method. When a drug with such a skeleton therein shall be administered, therefore, it can be expected that a distribution of the drug in the living body changes to increase its pharmacological activity or express a new pharmaceutical effect. Therefore, the compounds shown by Formula (I) are quite important as an intermediate for preparing various medicines and agricultural chemicals.

The compounds of Formula (I) can be synthesized through the reaction referred to before, for the compounds (IV).

DETAILED DESCRIPTION OF PREFERRED EMBODIMENTS

The invention will now be further explained in more detail and concrete with reference to Examples and Reference Examples.

EXAMPLE 1

1-Azonia-4,6-dimethylbicyclo[3.3.0]oct-1(5)-ene perchlorate

To a solution of bis(1-methylcyclopropyl)methanimine hydrochloride (0.044 g, 0.25 mmol) in 0.50 ml of dimethyl sulfoxide was added 0.061 g (0.50 mmol) of ammonium perchlorate. The mixture was heated with stirring at 100° C. for 16 hours. The solvent was distilled out in vacuo and ether was added to the residue. Precipitated crystals was obtained and recrystallized from ethanol to afford 0.27 g (Yield: 45%) of the desired compound.

$^1$H-NMR spectrum (DMSO-d$_6$) δ ppm:
1.24 (6H, d, J=7.32 Hz, CH$_3$ x 2),
2.4–2.7 (4H, m,

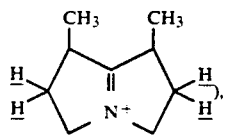

3.2–3.4 (2H, m,

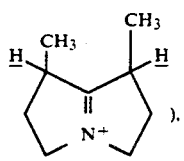

3.8–4.0 (4H, m, 0

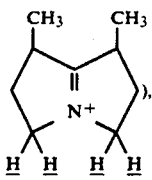

MS spectrum (EI/DI) m/z:
138 (M-ClO$_4^-$)$^+$, 136 (base peak).
MS spectrum [CI/DI (i-Bu)] m/z:
138 [(M-ClO$_4^-$)+1]$^+$, 138 (base peak).

EXAMPLE 2

1-Azoniabicyclo[3.3.0]oct-1(5)-ene perchlorate

To a solution of dicyclopropylmethanimine hydrochloride (1.00 g, 6.87 mmol) in 6.0 ml of dimethyl sulfoxide was added 1.68 g (1.37 mmol) of ammonium perchlorate. The mixture was heated with stirring at 100°

C. for 6 hours. The solvent was distilled out in vacuo and isobutyl alcohol (6 ml) was added to the residue. Precipitated crystals was obtained and recrystallized from ethanol to afford 1.15 g (Yield: 80%) of the desired compound.

Melting point 240°–244° C.

$^1$H-NMR spectrum (DMSO-d$_6$) δ ppm:
2.4–2.6 (4H, m)

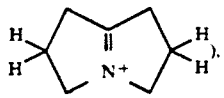

2.9–3.0 (4H, m),

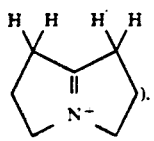

3.8–3.9 (4H, m),

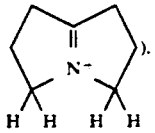

IR spectrum ($\nu_{max}^{KBr}$) cm$^{-1}$:
2980, 2890 (C-H), 1695 (C=N), 1100 (ClO$_4$).
MS spectrum (EI/DI) m/z:
110 (M-ClO$_4^-$)$^+$, 108 (base peak).
MS spectrum [CI/DI (i-Bu)] m/z:
111 [(M-ClO$_4^-$)+1]$^+$, 110 (base peak).

EXAMPLE 3

1-Azoniabicyclo[3.3.0]oct-1(5)-ene perchlorate

To a solution of dicyclopropylmethanimine hydrobromide (1.00 g, 5.26 mmol) in 6.0 ml of dimethyl sulfoxide was added 1.29 g (10.5 mmol) of ammonium perchlorate. The mixture was heated with stirring at 100° C. for 1 hour. The solvent was distilled out in vacuo and isobutyl alcohol was added to the residue. Precipitated crystals was obtained and recrystallized from ethanol to afford 0.90 g (Yield: 82%) of the desired compound.

The spectrum of the compound were identified to those of the product of Example 2.

EXAMPLE 4

1-Azoniabicyclo[3.3.0]oct-1(5)-ene chloride

A solution of dicyclopropylmethanimine hydrochloride (1.00 g, 6.87 mmol) in 6.0 ml of dimethyl sulfoxide was heated with stirring at 100° C. for 4 hours. The solvent was distilled out in vacuo and isobutyl alcohol (6 ml) was added to the residue. Precipitated crystals was obtained and dried in vacuo to afford 0.55 g (Yield: 55%) of the desired compound.

$^1$H-NMR spectrum (DMSO-d$_6$) δ ppm:
2.4–2.6 (4H, m)

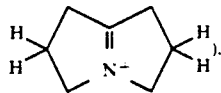

2.9–3.0 (4H, m,

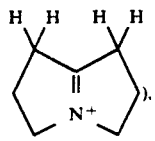

3.8–3.9 (4H, m,

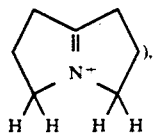

MS spectrum (EI/DI) m/z:
110 (M-ClO$_4^-$)$^+$, 108 (base peak).
MS spectrum [CI/DI (i-Bu)] m/z:
111[(M-ClO$_4^-$) + 1]$^+$, 110 (base peak).

EXAMPLE 5

1-Azoniabicyclo[3.3.0]oct-1(5)-ene bromide

A solution of dicyclopropylmethanimine hydrobromide (1.00 g, 5.26 mmol) in 6.0 ml of dimethyl sulfoxide was heated with stirring at 100° C. for 1 hour. The solvent was distilled out in vacuo and of isobutyl alcohol (8 ml) was added to the residue. Precipitated crystals was obtained and dried in vacuo to afford 0.56 g (Yield: 56%) of the desired compound.

$^1$H-NMR spectrum (DMSO-d$_6$) δ ppm:
2.4–2.6 (4H, m)

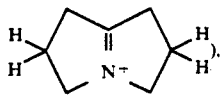

2.9–3.0 (4H, m),

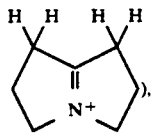

3.8–3.9 (4H, m),

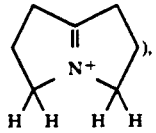

MS spectrum (EI/DI) m/z:
110 (M-ClO$_4^-$)$^+$, 108 (base peak).
MS spectrum [CI/DI (i-Bu)] m/z:
111[(M-ClO$_4^-$) + 1]$^+$, 110 (base peak).

EXAMPLE 6

1-Azoniabicyclo[3.3.0]oct-1(5)-ene tetrafluoroborate

To a solution of dicyclopropylmethanimine hydrobromide (0.200 g, 1.05 mmol) in 2.0 ml of dimethyl sulfoxide was added 0.232 g (2.10 mmol) of ammonium tetrafluroborate. The mixture was heated with stirring at 100° C. for 2 hours. The solvent was distilled out in vacuo and isobutyl alcohol was added to the residue. Precipitated crystals was obtained and recrystallized from ethanol to afford 0.17 g (Yield: 82%) of the desired compound.

$^1$H-NMR spectrum (DMSO-$d_6$) δ ppm:
2.4-2.6 (4H, m

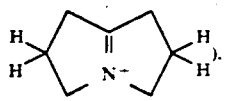

2.9-3.0 (4H, m,

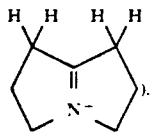

3.8-4.0 (4H, m,

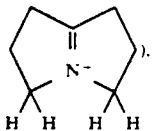

MS spectrum (EI/DI) m/z:
110 (M-ClO$_4^-$)$^+$, 108 (base peak).
MS spectrum [CI/DI (i-Bu)] m/z:
111[(M-ClO$_4^-$)+1]$^+$, 110 (base peak).

EXAMPLE 7

Bis(1-azoniabicyclo[3.3.0]oct-1(5)-ene) sulfate

To a solution of dicyclopropylmethanimine hydrobromide (0.200 g, 1.05 mmol) in 5.0 ml of dimethyl sulfoxide was added 0.139 g (1.05 mmol) of ammonium sulfate. The mixture was heated with stirring at 100° C. for 2 hours. The solvent was distilled out in vacuo and isobutyl alcohol was added to the residue. Precipitated crystals was obtained and recrystallized from ethanol to afford 0.10 g (Yield: 62%) of the desired compound.

$^1$H-NMR spectrum (DMSO-$d_6$) δ ppm:
2.4-2.6 (4H, m

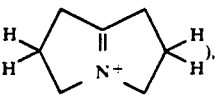

2.9-3.0 (4H, m,

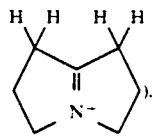

3.8-4.0 (4H, m,

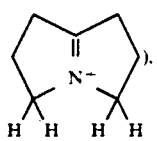

MS spectrum (EI/DI) m/z:
110 (M-ClO$_4^-$)$^+$, 108 (base peak).
MS spectrum [CI/DI (i-Bu)] m/z:
111[(M-ClO$_4^-$)+1]$^+$, 110 (base peak).

EXAMPLE 8

1-Azoniabicyclo[3.3.0]oct-1(5)-ene perchlorate

To a solution of dicyclopropylmethanimine perchlorate (0.200 g, 0.954 mmol) in 1.0 ml of dimethyl sulfoxide was added 0.0510 g (0.0954 mmol) of ammonium chloride. The mixture was heated with stirring at 100° C. for 3 hours. The solvent was distilled out in vacuo and isobutyl alcohol was added to the residue. Precipitated crystals was obtained and recrystallized from ethanol to afford 0.16 g (Yield: 82%) of the desired compound.

The spectrum of the compound were identical to those of the product of Example 2.

EXAMPLE 9

1-Azonia-4-methylbicyclo[3.3.0]oct-1(5)-ene perchlorate

To a solution of 1-cyclopropyl-1-(1-methylcyclopropyl)methanimine hydrochloride (0.060 g, 0.38 mmol) in 0.60 ml of dimethyl sulfoxide was added 0.088 g (0.75 mmol) of ammonium perchlorate. The mixture was heated with stirring at 100° C. for 20 hours. The solvent was distilled out in vacuo and ether was added to the residue. Precipitated crystals was obtained and recrystallized from ethanol to afford 0.36 g (Yield: 43%) of the desired compound.

$^1$H-NMR spectrum (DMSO-$d_6$) δ ppm:
1.36 (3H, d, J=7.33 Hz, CH$_3$),
2.5-2.8 (4H, m

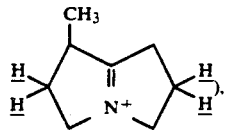

2.9-3.1 (2H, m,

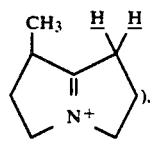

3.2-3.4 (1H, m,

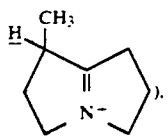

3.8–4.1 (4H, m,

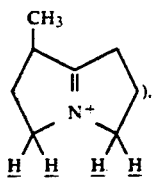

MS spectrum [CI/DI (i-Bu)] m/z:
125[(M-ClO$_4^-$)+1]$^+$, 85 (base peak).

REFERENCE EXAMPLE 1 (PREPARATION OF RAW MATERIAL)

Dicyclopropylmethanimine hydrochloride

To a solution of dicyclopropylketone (1.00 g, 9.09 mmol) in 30 ml of benzene was added in dropwise 0.55 ml (5.0 mmol) of titanium tetrachloride with stirring at 5° C. under ammonia atmosphere. After stirred the mixture for 5 hours under ammonia atmosphere, the solution was allowed warm up to 20° C., while bubbling hydrogen chloride gas into the mixture. Then the reaction mixture was concentrated in vacuo and crystal residue was suspended in 50 ml of chloroform. The solid was separated and the filtrate was concentrated. Ether (50 ml) was added to the concentrate and then the precipitated crystals were collected and dried to afford 0.73 g (Yield: 55%) of the desired compound.

Melting point: 125°–127° C.
$^1$H-NMR spectrum (CDCl$_3$) δ ppm:
1.3–1.5 (8H, m, CH$_2$x 4),
1.9–2.0 (2H, m, CH x2),
11.5 (2H, brs, $^+$NH$_2$).
IR spectrum (ν$_{max}^{KBr}$) cm$^{-1}$:
2920 (C—H), 1650 (C=N$^+$H$_2$).
MS spectrum (EI/DI) m/z:
109[(M-HCl)$^+$], 94 (base peak).

REFERENCE EXAMPLE 2 (CHECK ON REACTIVITY OF OBJECTIVE COMPOUND)

Preparation of 5-cyano-1-azabicyclo[3.3.0]octane

To a solution of potassium cyanide (0.191 g, 2.86 mmol) in 1.0 ml of water was added over 20 minutes 0.284 g (1.35 mmol) of 1-azoniabicyclo[3.3.0]oct-1(5)-ene (Example 3). The mixture was stirred at 20° C. for 1 hour. To the reaction mixture was added 2 ml of water and extracted with methylene chloride (3×10 ml). The combined organic layers were dried over anhydrous sodium sulfate and the solvent was distilled out in vacuo to afford 171 mg (Yield: 93.3%) of the desired compound.

Boiling point: 93°–95° C. (5 mmHg).
$^1$H-NMR spectrum (CDCl$_3$) δ ppm:
1.8–2.4 (8H, m

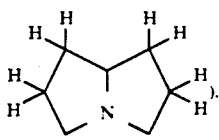

2.5–2.6 (2H, m,

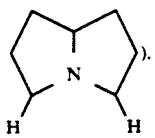

3.2–3.3 (2H, m,

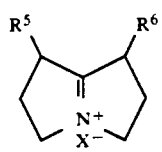

IR spectrum (ν$_{max}^{neat}$) cm$^{-1}$:
2950 (C—H), 2230 (C≡N).

What is claimed is:

1. 1-Azonia-4,6-disubstituted-bicyclo-[3.3.0]oct-1(5)-ene salt derivatives shown by the formula of

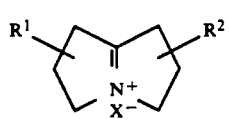

(I)

wherein X is a halogen atom, ClO$_4$, NO$_3$, BF$_4$, R$^3$SO$_3$, (SO$_4$)$_{0.5}$ or CW$_3$CO$_2$, and R$^5$ and R$^6$ are same or different hydrocarbon group with 1–10 carbon atoms, or one of R$^5$ and R$^6$ represents hydrogen atom and the other is the hydrocarbon group with 2–10 carbon atoms.

2. 1-Azonia-4,6-disubstituted-bicyclo[3.3.0]oct-1(5)-ene salt derivative as claimed in claim 1, wherein the derivative is 1-azonia-4,6-dimethylbicyclo[3.3.0]oct-1(5)-ene perchlorate.

3. A process for the preparation of 1-azoniabicyclo[3.3.0]oct-1(5)-ene salt derivatives of the formula (IV)

wherein X is a halogen atom, ClO$_4$, NO$_3$, BF$_4$, R$^3$SO$_3$, (SO$_4$)$_{0.5}$ or CW$_3$CO$_2$ , and R$^1$ and R$^2$ are same or different and each being hydrogen atom or hydrocarbon group with 1–10 carbon atoms, which comprises the step of heating in a solvent a dicyclopropylmethanimine salt derivative of the formula

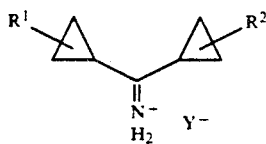

(II)

wherein $R^1$ and $R^2$ have the meanings referred to above, and Y is a halogen atom, $ClO_4$, $NO_3$, $BF_4$, $R^3SO_3$, $(SO_4)_{0.5}$ or $CW_3CO_2$, solely or with an ammonium salt of the formula $$NR^4_4Z \qquad (III)$$

wherein Z is a halogen atom, $ClO_4$, $NO_3$, $BF_4$, $R^3SO_3$, $(SO_4)_{0.5}$ or $CW_3CO_2$ and $R^4$ is a hydrocarbon group with 1–10 carbon atoms, in case of that the symbol Y represents the halogen atom, $R^3SO_3$ or $(SO_4)_{0.5}$; or with the ammonium salt of Formula (III), wherein Z is the halogen atom, $R^3SO_3$ or $(SO_4)_{0.5}$, in case of that Y represents the radical other than the halogen atom, $R^3SO_3$ or $(SO_4)_{0.5}$.

* * * * *